(12) United States Patent
Weimann

(10) Patent No.: US 10,272,125 B2
(45) Date of Patent: *Apr. 30, 2019

(54) TRANSDERMAL DELIVERY OF CANNABIDIOL WITH OTHER ACTIVE MOIETIES INCLUDING CANNABINOIDS

(71) Applicant: LIFE TECH GLOBAL, LLC, Irvine, CA (US)

(72) Inventor: Ludwig Weimann, San Diego, CA (US)

(73) Assignee: Life Tech Global, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/265,823

(22) Filed: Sep. 14, 2016

(65) Prior Publication Data

US 2017/0071870 A1    Mar. 16, 2017

Related U.S. Application Data

(60) Provisional application No. 62/283,890, filed on Sep. 14, 2015.

(51) Int. Cl.
| | | |
|---|---|---|
| *A61K 9/70* | (2006.01) | |
| *A61K 31/05* | (2006.01) | |
| *A61K 31/352* | (2006.01) | |
| *A61K 36/185* | (2006.01) | |
| *A61K 47/10* | (2017.01) | |
| *A61K 47/12* | (2006.01) | |
| *A61K 47/32* | (2006.01) | |
| *A61K 47/34* | (2017.01) | |
| *A61K 47/38* | (2006.01) | |

(52) U.S. Cl.
CPC .......... *A61K 36/185* (2013.01); *A61K 9/7053* (2013.01); *A61K 9/7084* (2013.01); *A61K 31/05* (2013.01); *A61K 31/352* (2013.01)

(58) Field of Classification Search
CPC .... A61K 9/703; A61K 9/7053; A61K 9/7084; A61K 31/352; A61K 47/38
See application file for complete search history.

(56) References Cited

U.S. PATENT DOCUMENTS

| | | | | |
|---|---|---|---|---|
| 4,573,996 A | * | 3/1986 | Kwiatek | A61K 9/7084 424/434 |
| 5,079,008 A | * | 1/1992 | Sinnreich | A61K 9/7053 424/447 |
| 5,925,372 A | * | 7/1999 | Berner | A61K 9/7069 424/447 |
| 5,948,433 A | * | 9/1999 | Burton | A61K 9/7053 424/448 |
| 6,328,992 B1 | * | 12/2001 | Brooke | A61K 9/7061 424/443 |
| 9,044,390 B1 | * | 6/2015 | Speier | A61K 36/00 |
| 2006/0029654 A1 | * | 2/2006 | Cassel | A61K 31/24 424/449 |
| 2008/0233180 A1 | * | 9/2008 | Zeltman | A61K 9/7061 424/449 |
| 2008/0274167 A1 | * | 11/2008 | Muller | A61K 9/7092 424/449 |
| 2009/0005722 A1 | * | 1/2009 | Jennings-Spring | A61F 13/00021 604/20 |
| 2009/0291128 A1 | * | 11/2009 | Stinchcomb | A61K 9/0014 424/449 |
| 2011/0052694 A1 | * | 3/2011 | Stinchcomb | A61K 9/0021 424/484 |
| 2011/0129521 A1 | * | 6/2011 | Epner | A61K 31/4406 424/449 |
| 2011/0245288 A1 | * | 10/2011 | Stinchcomb | C07D 489/12 514/282 |
| 2014/0188057 A1 | * | 7/2014 | Sivaraman | A61K 9/7084 604/307 |

FOREIGN PATENT DOCUMENTS

| | | | | |
|---|---|---|---|---|
| WO | WO 2008024408 A2 | * | 2/2008 | ........... A61K 9/7061 |
| WO | WO 2015068052 A2 | * | 5/2015 | ........... A61K 31/352 |

OTHER PUBLICATIONS

Cannabidiol (CBD) Pre-Review Report Agenda Item 5.2, Expert Committee on Drug Dependence, Thirty-ninth Meeting, Geneva, Nov. 6-10, 2017, World Health Organization.

\* cited by examiner

*Primary Examiner* — Doan T Phan
(74) *Attorney, Agent, or Firm* — Patnstr, APC; Tom Brody; Peter Jon Gluck, Esq.

(57) ABSTRACT

Transdermal delivery devices for the delivery of cannabidiol (CBD) and related moieties are shown and described. In a reservoir-patch design, a microporous, hydrophilic membrane and a backing define a reservoir that houses a mixture of CBD, a polar liquid, and a gelling agent. In a monolithic design, a release liner is coated with a mixture of CBD and a PIB or amine-compatible silicone skin adhesive laminated to the backing material. In using CBD as a pure compound or as one to combine with other moieties, the invention is able to control delivery better than the prior art.

23 Claims, 5 Drawing Sheets

TRANSDERMAL DELIVERY OF CANNABIDIOL WITH OTHER ACTIVE MOIETIES INCLUDING CANNABINOIDS

CROSS REFERENCE TO RELATED APPLICATIONS

The instant application claims full priority, including all Paris Convention and related rights from U.S. Provisional Patent Application No. 62/283,890.

FIELD

This disclosure relates to devices and methods for the transdermal delivery of cannabidiol, among other desiderata using improved patch-technology, by way of a liquid saturated matrix and/or saturated alcohol solution.

BACKGROUND

Cannabidiol (CBD) ($C_{21}H_{30}O_2$, CAS Registry No. 13956-29-1) is an active cannabinoid present in *cannabis*, a genus of flowering plants that includes *Cannabis sativa, Cannabis indica*, and *Cannabis ruderalis*. Other cannabinoids include tetrahydrocannabinol (THC), tetrahydrocannabinolic acid (THC-a), cannabinol (CBN), and cannabichromene (CBC). Research shows that the combinations of various moieties produces much of the desired medical and other effect solicited by the industry at large.

Surprisingly, THC is but a factor not the prime mover in this equation, as most literature and patent literature has focused upon.

CBD and THC-a are main components of the marijuana plant. For decades, the CBD content in marijuana plants was very low (below 5%), and all efforts were directed toward increasing the content of psychoactive component of marijuana—THC—for recreational purposes. Recently however, extensive medical research of medicinal attributes of marijuana suggests that CBD is the most important a non-psychoactive component of marijuana that possesses a wide range of therapeutic benefits.

Growers of marijuana developed new strands of the plant with high content of CBD. When subjected to an extraction process the yield of CBD in the concentrated extract (oil, shatters) may approach 70% by weight and higher. The increased CBD concentration made it possible to formulate products consumed as edibles, tinctures capsules, lotions, and creams containing medicinal quantities of CBD. The CBD in such products has been used for serious therapeutic medical treatments such as: reversing alcohol induced brain damage, treating of severe social anxiety, turning off the cancer gene found in metastasis, effectively treating schizophrenia and epilepsy, treating neurogenerative disorders or even slowing down Parkinson's disease and Alzheimer's disease.

Successful use of CBD for medical treatments such as the foregoing depends on the dose of the medicine, reducing side effects, and patient compliance. Orally taken CBD is exposed to the gastric environment and liver, which metabolizes the medicine and thereby lowers its bioavailability. Creams and lotions act for a short time being rubbed off by cloth and washed off.

Transdermal delivery is an alternate route for delivering potent medicines. It circumvents the gastric system, and therefore, the medical substance does not cause liver damage and has increased bioavailability. In particular, children are most susceptible to such damage and may particularly benefit from the transdermal delivery of CBD because transdermal delivery allows for the controlled, sustained delivery of CBD to the body for at least 24 hrs—and possibly for 2-3 days—without damaging young livers.

Transdermal delivery of cannabinoids has been proposed. However, known reservoir-style transdermal devices have used liquid carriers and/or hydrophobic rate-controlling membranes and carriers which have undesirably limited the rate of mass transfer of CBD through the skin. In addition, certain known reservoir-style devices require an additional adhesive coated overlay to hold the device in place on the wearer's skin.

Monolithic transdermal devices (also known as "drug-in-adhesive" devices) for delivering cannabinoids have also been proposed. However, the adhesive used in such known devices has typically limited the rate of mass transfer of CBD to the skin.

Thus, a need has arisen for a transdermal device for delivering CBD. Since the present inventor has experimented and realized key aspects of delivery, the patches developed and related technology are known to constitute progress in science and the useful arts subject to patent protection.

OBJECTS AND SUMMARY OF THE INVENTION

Briefly stated, transdermal delivery devices for the delivery of cannabidiol (CBD) are shown and described. In a reservoir-patch design, a microporous, hydrophilic membrane and a backing define a reservoir that houses a mixture of CBD, a polar liquid, and a gelling agent. The hydrophilic membrane is coated with an amine-compatible silicone skin adhesive. In a monolithic design, a release liner is coated with a mixture of CBD and a PIB or amine-compatible silicone skin adhesive laminated to the backing material. In using CBD as a pure compound or as one to combine with other moieties, the invention is able to control delivery better than the prior art. Construction of the Transdermal patch of reservoir type is also taught.

According to embodiments, there is provided a transdermal patch formulation comprising a reservoir in the shape of a "ravioli" constructed with microporous hydrophilic or hydrophobic membrane on one side and occlusive film on other side, further comprising thixotropic alcohol or alcohol/water solution gelled with hydroxyalkyl cellulose containing CBD at high concentration ranging from at least about 1% to 50% CBD.

According to embodiments there is provided a transdermal reservoir patch formulation comprising a reservoir containing thixotropic alcohol or alcohol/water solution gelled with hydroxyalkyl cellulose and containing CBD at a high concentration, ranging from 1% to 50% and skin penetration enhancers in a concentration range of 0% to 10%. In embodiments, there is provided a transdermal patch formulation comprising a reservoir in the shape of a "ravioli" constructed with microporous hydrophilic or hydrophobic membrane on one side and occlusive film on other side. What is provided is a transdermal reservoir patch formulation as above, further comprising thixotropic alcohol or alcohol/water solution gelled with hydroalkylcellulose containing CBD at high concentration ranging from at least 1% to 50% CBD. The disclosure provides a device for the transdermal delivery of cannabidiol (CBD), comprising a backing; a release liner; a mixture of an adhesive and a therapeutically effective amount of cannabidiol coated on the release liner, wherein the mixture includes tetrahydrocannabinol (THC), tetrahydrocannabiniolic acid (THC-a), cannabinol (CBN), and cannabichromene (CBD); wherein the adhesive comprises a polyisobutylene adhesive having a viscosity-average molecular weight ranging from about 30,000 to about 70,000 Daltons, and the mixture has a first surface adhered to the backing and a second, skin-adhering surface to which the release liner is removably adhered. Also, what is provided is the above device, wherein the adhesive has a viscosity at 20 degrees C. ranging from about 1000 mPa-s to about 3000 mPa-s. Also, where is provided the above transdermal patch, further comprising at least one mechanisms of CBD and THC delivery from liquid saturated matrix (E+OH+water); and use of hemp oil in delivering CBD from saturated alcohol solution, because of being too viscous for use with saturated liquid matrix.

According to embodiments there is provided a transdermal patch formulation comprising a reservoir in shape of "ravioli" constructed with microporous hydrophilic or hydrophobic membrane on one side and occlusive film on other side where the microporous membrane is coated with thin layer of silicone adhesive; said patch of 20 cm² effective to deliver 1.5 mg/20 cm²×20 cm², 30 mg/day of CBD systemically.

According to embodiments there is provided a device for the transdermal delivery of cannabidiol and other moieties, comprising, in combination; a backing attached to a hydrophilic, porous membrane to define an enclosed reservoir between the backing and the hydrophilic, porous membrane, wherein the porous membrane has a first side with a skin adhesive and a second side facing the interior of the reservoir; a preparation comprising a therapeutically effective amount of cannabidiol (CBD) and an organic polar liquid carrier contained in the reservoir, wherein the preparation includes tetrahydrocannabinol (THC), tetrahydrocannabinolic acid (THC-a), cannabinol (CBN), and cannabichromene (CBC); and, a release liner attached to the first side of the hydrophilic porous membrane, wherein the release liner is selectively removable from the first side of the hydrophilic porous membrane to expose the skin adhesive.

According to embodiments there is provided a method of transdermally delivering cannabidiol (CBD) to a person, comprising; providing a device housing at least one of a liquid saturated matrix and a saturated alcohol solution; removing the release liner from the first side of the porous, hydrophilic membrane; contacting the first side of the porous, hydrophilic membrane with the person's skin; and maintaining the device in contact with the person's skin for a period of time sufficient to deliver the therapeutically effective amount of cannabidiol to the patient.

According to embodiments there is provided a device for the transdermal delivery of cannabidiol (CBD), comprising; a backing, a mixture of an adhesive and a therapeutically effective amount of cannabidiol coated on the backing, wherein the mixture includes a least one of tetrahydrocannabinol (THC), tetrahydrocannabinolic acid (THC-a), cannabinol (CBN), and cannabichromene (CBC), vitamin B12, Terpenes and Beta-carylophenol; wherein the adhesive comprises an amine-compatible silicone adhesive and the mixture has a first surface adhered to the backing and a second, skin-adhering surface, a release liner removably attached to the second, skin adhering surface of the mixture.

BRIEF DESCRIPTION OF THE DRAWINGS

Various preferred embodiments are described herein with references to the drawings in which merely illustrative views are offered for consideration, whereby.

DETAILED DESCRIPTION

Figure 1:
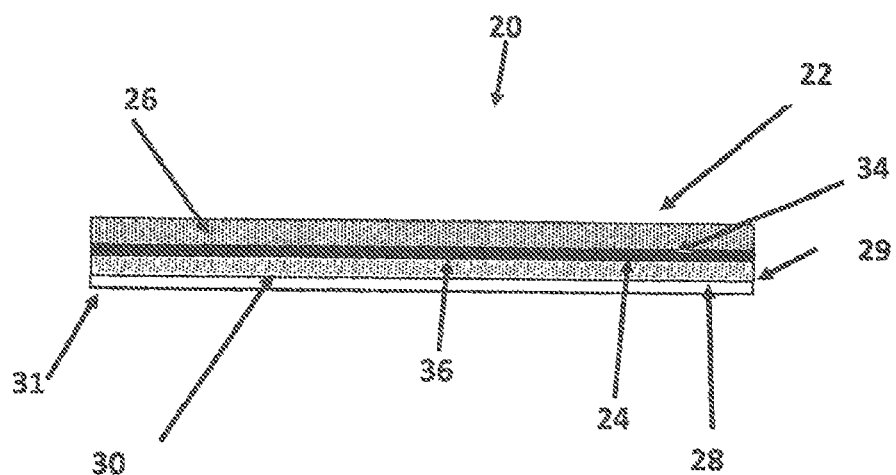
FIG. 1 is a side cross-sectional view of a reservoir-style transdermal device for delivering CBD to a wearer's skin.

The present inventor has discovered that success of medical treatment depends on the dose of the medicine, substance absorbency and potency, low side effects and patient compliance. When taken orally, CBD is exposed to and broken down by the gastric environment of the digestive trace and is then subject to liver first-pass that further metabolizes the substance, lowering its bioavailability. Creams and lotions are effective but act for a short time and have a higher chance of being washed or rubbed off.

Transdermal patch delivery is an alternate method of delivering potent medicines. Patch delivery circumvents the gastric system and therefore the medical substance is not subject to the digestive system of the liver first-pass effect. Children, the elderly, and those with compromised immune systems or those who are taking multiple medications who are most vulnerable to organ damage from ingested substances, would benefit from using transdermal patch delivery that provides a safe, controlled and sustained delivery of CBD for at least 24 hours and up to 72 hours.

Preliminary Example and Patch Basics for Monolithic Version:

| Transdermal monolithic CBD patch formulation: | |
|---|---|
| Adhesive polymer: | 60-95 |
| CBD: | 5-20 |
| Penetration enhancer: | 0-20 |

-continued

Transdermal monolithic CBD patch formulation:

| | |
|---|---|
| Adhesive polymer: | Acrylate from Hankel, Silicone from Dow Corning, PIB from BASF |
| CBD: | pure crystalline powder |
| Penetration enhancer: | Oleic acid, IPP, DMSO, 1,2 PG, IPM |

In this example, the dry adhesive matrix is 30-50 microns thick. The area of the patch can be square or oval. The best size of the patch is 20 cm² by 40 cm².

How the Monolithic CBD Patch Works:
1. CBD is dissolved in ethyl alcohol or 1,2 PG and mixed into the adhesive solution and penetration enhancer is added if needed.
2. Adhesive mix is dispensed on the release liner by means of "knife-over-roll" coating method and dried in the oven at drying time from 1 min to 3 min or until all residual solvents are below 1 ppm.
3. Dried adhesive film is laminated to the backing film by means of nipping and edges are slit for farther die cutting of the patches.
4. The laminate is placed on the die cutting machine and proper size patches are cut and later packaged in the pouches and boxes.

How CBD is Delivered from the Patch Formulation to the Body Through the Skin:
Formulations of monolithic patches were prepared by solubilizing CBD in different adhesives and CBD transdermal flux was performed through human cadaver skin using Franz Diffusion Cell method. We found the highest transdermal flux of CBD from a formulation that comprises PIB adhesive and 10% CBD. This suggests that a patch measuring 20 cm² would deliver a daily systemic dose of ~5 mg of CBD (See FIG. 1-7).

Exemplary Monolithic Patch Invention Formulations:
1. 10% CBD in EtOH
2. 10% CBD in EtOH/H₂O 9/1
3. Penetration enhancers: 1,2 PG, IPP oleic acid, DMSO Formulation Preparation:
1. CBD is dissolved in Ethanol to make a 10% solution and Hydroxy ethyl cellulose is added to increase viscosity of the solution.
2. 300 ☐00 solution and Hydroxy ethyl cellulose is ada microporous membrane (of 0.2 ☐icroporous membrane (of 0.2 yl cellulose is added to increase
3. Overlay adhesive patch is placed over the reservoir, which forms an island in the middle. Overlay assures adhesion of the reservoir to the skin.

Noted Improvements:
1. CBD delivered from invention patch formulations through skin is safer because it circumvents the gastric system and liver first-pass, avoiding toxic side effects and increasing bioavailability of the compound
2. CBD Patch has better patient compliance in comparison to pills, edibles, tinctures and creams.

Described below are examples of transdermal delivery devices for delivering CBD through the epidermis of a wearer of the device. Both reservoir-style, and monolithic-style devices are described. In the reservoir style device, a reservoir comprising a solution of CBD (which may be present as substantially pure CBD or an oil extract of a *cannabis* plant which comprises CBD and other cannabinoids) and a liquid carrier is provided and is defined between a hydrophilic, porous membrane and a backing. One side of the hydrophilic, porous backing is coated with a skin adhesive that is covered with a release liner. To use the device, the user removes the release liner and contacts the skin adhesive-side of the membrane with the skin to affix the device to the body. Preferred skin adhesives include amine-compatible, silicone adhesives. The phrase "amine-compatible" refers to the fact that the adhesive is substantially non-reactive with amines. Many drugs are amines that bond with hydrogen donors. Silicone adhesive polymers typically have OH groups that are hydrogen donors. When mixed with drugs that have NH groups (amines) or OH groups (like cannabidiol) that can accept hydrogen, the drug and silicone polymer will bond through hydrogen bonding, which retards the diffusion of drug molecules from the adhesive matrix. To avoid that diffusion retardation, the OH groups of the silicone polymer, are capped with methyl groups. Such silicone adhesive will be called "amine compatible" which means they are essentially chemically neutral.

The CBD diffuses through the hydrophilic, porous membrane and the skin adhesive and into the user's skin.

In a first monolithic-style device, a skin adhesive is mixed with the CBD (which may be present as substantially pure CBD or an oil extract of a *cannabis* plant which comprises CBD and other cannabinoids) to define a substantially monolithic mixture of adhesive and CBD. The skin adhesive is coated on a backing that is preferably occlusive. The skin adhesive is preferably an amine-compatible silicone adhesive.

In a second monolithic-style device, a skin adhesive is mixed with the CBD (which may be present as substantially pure CBD or an oil extract of a *cannabis* plant which comprises CBD and other cannabinoids) to define a substantially monolithic mixture of adhesive and CBD. The skin adhesive is preferably a polyisobutylene adhesive having a viscosity-average molecular weight ranging from about 30,000 Daltons to about 70,000 Daltons, preferably, from about 35,000 Daltons to about 65,000 Daltons, and more preferably from about 40,000 Daltons to about 60,000 Daltons.

The following outlines the manufacture of an embodiment of device. CBD is dissolved in ethyl alcohol or 1,2-propylene glycol (1,2 PG) and mixed into the adhesive solution and penetration enhancer is added if needed. Adhesive mix is dispensed on the release liner by means of "knife-over-roll" coating method and dried in the oven at drying time from 1 min to 3 min or until all residual solvents are below 1 ppm. Dried adhesive film is laminated to the backing film by means of nipping and edges are slit for further die cutting of the patches. The laminate is placed on the die cutting machine and proper size patches are cut and later packaged in the pouches and boxes.

Hydrogel patches are provided. In embodiments, hydrogel comprises polyvinylalcohol hydrogel; silicone hydrogel; polyvinylalcohol/dextran hydrogel; alginate hydrogel; alginate-pyrrole hydrogel; gelatin/chitosan hydrogel; polyacrylic acid hydrogel; photo crosslinked polyacrylic acid hydrogel; amidated pectin hydrogel; pectin hydrogel; gelatin hydrogel; polyethylene glycol (PEG) hydrogel; carboxymethylcellulose/gelatin hydrogel; chitosan hydrogel, as well as mixtures thereof, or copolymers thereof, and the like.

Referring to FIG. 1, a reservoir-style transdermal delivery device 20 for the transdermal delivery of CBD is depicted. Reservoir-style transdermal delivery device 20 comprises a backing 22 and a hydrophilic, porous membrane 24. The backing 22 and hydrophilic, porous membrane 24 are attached to one another so as to define a closed volume which acts as a reservoir 26. A preparation 27 comprising CBD, a liquid carrier, and a gelling agent is disposed in the reservoir 26. First side 34 of the hydrophilic, porous membrane 24 is in contact with the preparation 27. A second side 36 of the hydrophilic, porous membrane 24 faces away from backing 22 and is coated with a skin adhesive 30. The skin adhesive 30 is preferably formulated to adhere the device 20 to the user's skin for a period of no less than about 24 hours while avoiding appreciable skin irritation to the user's skin. Preferred skin adhesives 30 include amine-compatible, silicone, pressure sensitive adhesives. In certain examples, an amine-compatible silicone skin adhesive 30 is provided which comprises a trimethylsiloxy end-capped reaction product of a silanol end-blocked polydimethylsiloxane and a silicate resin. The skin adhesive is preferably provided as an organic solvent solution comprising from about 50 percent to about 70 percent by weight of solid adhesive in an organic solvent like heptane or ethyl acetate and having a viscosity at 20° C. of from about 400 mPa-s to about 1300 mPa-s, preferably from about 450 mPa-s to about 1250 mPa-s, and more preferably from about 500 mPa-s to about 1200 mPa-s.

A first surface 29 of a release liner 28 is releasably adhered to skin adhesive 30, and a second surface 31 of release liner 28 faces away from skin adhesive 30. Suitable release liners include occlusive polymeric films, such as polyester, polypropylene, coated with a release coating that is releasably adherable to silicone, polyisobutylene, and silicone adhesives. Suitable release coatings on first surface 29 of release liner 28 include fluoropolymers and silicone polymers. Commercially-available, coated release liners that are suitable for use as release liner 28 include Scotchpak 1022, 9741, 9744, 9748, and 9755 supplied by 3M of Minneapolis, Minn., and FRA 314 and 315 supplied by Fox River Co. To use the reservoir transdermal device 20, release liner 28 is peeled away from skin adhesive 30, thereby exposing skin adhesive 30, and the device 20 is applied so that the skin adhesive 30 contacts the user's skin.

Suitable examples of such amine-compatible silicone adhesives include the BIO-PSA 7-4301 and 7-4302 skin adhesives supplied by Dow Corning. BIO-PSA 7-4301 is a high tack, amine-compatible silicone adhesive in heptane available with a solids content of 60 percent and 70 percent and corresponding viscosities at 20° C. of 450 mPa-s and 1600 mPa-s. BIO-PSA 7-4302 is a high tack, amine-compatible silicone adhesive in ethyl acetate with a solids content of 60 percent by weight and a viscosity of 1200 mPa-s at 20° C. The skin adhesive 30 is coated to a thickness per unit area on the membrane 24 that is preferably from about 10 to about 20 g/m$^2$, more preferably from about 12-18 g/m$^2$, and still more preferably from about 14-16 g/m$^2$.

Hydrophilic, porous membrane 24 preferably has a mean flow pore size of no more than about 1 micron, preferably not more than about 0.8 microns, still more preferably no more than about 0.4 microns, and even more preferably no more than about 0.2 microns. At the same time, porous membrane 24 preferably has a mean flow pore size of no less than about 0.02 microns, more preferably no less than about 0.04 microns, still more preferably no less than about 0.06 microns, and even more preferably no less than about 0.08 microns. The mean flow pore size may be determined in accordance with the method set forth at page 17, line 22 to page 18, line 4 of published PCT Application WO2010072233, the entirety of which is hereby incorporated by reference.

In the same or other examples, hydrophilic porous membrane 24 preferably has a porosity of at least about 60 percent, more preferably at least about 65 percent, and still more preferably at least about 70 percent. At the same time, hydrophilic porous membrane 24 preferably has a porosity of no more than about 90 percent, more preferably no more than about 85 percent, and still more preferably no more than about 80 percent. Porosity values may be calculated as described at page 7, lines 24 to 27 of WO2010072233.

In the same or other examples, hydrophilic porous membrane 24 preferably has a thickness of no more than about 50 microns, preferably no more than about 40 microns, and even more preferably no more than about 35 microns. At the same time, hydrophilic porous membrane 24 preferably has a thickness of no less than about 10 microns, more preferably no less than about 20 microns, and still more preferably no less than about 25 microns. Membrane thicknesses may be determined as described at page 18, lines 19-21 of WO2010072233.

In the same or other examples, hydrophilic porous membrane 24 preferably has an air permeability as determined by the Gurley Test Method (according to ISO 5636-5) that is preferably at least about 10 sec/50 ml, more preferably at least about 20 sec/50 ml, and still more preferably at least about 25 sec/50 ml. At the same time, hydrophilic porous membrane 24 preferably has an air permeability of no more than about 50 sec/50 ml, more preferably no more than about 40 sec/50 ml, and still more preferably no more than about 35 sec/50 ml.

In the same or other examples, hydrophilic porous membrane 24 preferably has a tensile strength in the machine direction as determined by ASTM D882-12 that is preferably at least about 10 MPa, more preferably at least about 15 MPa, and still more preferably at least about 20 MPa. In the same or other examples, the hydrophilic porous membrane 24 preferably has a percent elongation in the machine direction as determined by ASTM D882-12 that is preferably at least about 10 percent, more preferably at least about 15 percent, and still more preferably at least about 20 percent.

Hydrophilic porous membrane 24 preferably comprises at least one polymeric material. In one example, hydrophilic porous membrane 24 comprises a polyolefin polymer and a hydrophilic component that comprises a hydrophilic polymer and optionally, a surfactant. As used herein, the term "hydrophilic" when used to describe a porous membrane refers to a membrane that at 20° C. provides a water flux for demineralized water through the membrane of at least 0.5 liters/(m$^2$hbar).

The content of the polyolefin polymer is preferably less than or equal to 98 percent by weight based on the total dry weight of the membrane 24, and the content of the hydrophilic component(s) is preferably at least 2 weight percent based on the total dry weight of the membrane. In certain preferred examples, the membrane is formed by combining the polyolefin polymer with the hydrophilic components(s) and optional additives with a solvent to form a blend in the form of a gel, a solution, or a homogeneous mixture, followed by extruding the blend. Suitable polyolefins (such as polyethylene), hydrophilic components, and additives are described in WO2010072233.

One example of a commercially available hydrophilic, porous membrane that is suitable for use as hydrophilic, porous membrane 24 is supplied by Lydall Performance Materials B.V. under the name Evopor™ 5E02A. Evopor™ 5E02A is a porous hydrophilic membrane comprising a polyethylene support and a poly (ethyl vinyl) alcohol hydrophilic component.

As mentioned previously, preparation 27 comprises CBD and a liquid carrier. In certain examples, the polar organic liquid comprises a molecule having one or more carboxylic acid groups. In the same or other examples, the polar organic liquid comprises a molecule having one or more hydroxyl groups. Suitable polar organic liquids comprising one or more hydroxyl groups include those comprising between 2 and 30 carbon atoms per molecule, including without limitation, ethanol. Suitable polar organic liquids comprising one or more carboxylic acid groups include fatty acids, including without limitation oleic acid. Liquid carriers comprising ethanol and/or oleic acid are preferred, and liquid carriers comprising oleic acid are especially preferred. Suitable liquid carriers also include mixtures of polar organic liquids and water. Examples of such mixtures include mixtures of ethanol and water. In ethanol/water mixtures, the maximum concentration of water is preferably about ten (10) percent by weight of the total amount of ethanol and water.

Preparation 27 also may comprises a gelling agent which makes the preparation thixotropic. Suitable gelling agents include: sodium carboxymethyl cellulose, hydroxypropyl cellulose, hydroxyethyl cellulose, polyacrylic acid, methyl cellulose, xantam gum, etc. In certain examples, cellulose gelling agents such as hydroxyethyl cellulose are preferred. The gelling agent increases the viscosity of and provides structural integrity to preparation 27, which improves the ease of placing and retaining preparation 27 in reservoir 26 before the reservoir 26 is closed by heat sealing the hydrophilic, porous membrane 24 to the occlusive backing 22. The gelling agent is preferably pharmacologically inactive.

The CBD is present in a therapeutically effective amount in preparation 27. A "therapeutically effective amount" is an amount of CBD sufficient to achieve a desired therapeutic effect over a desired time period. The CBD may be provided as substantially pure CBD, such as in a powder form, or as part of an oil extract comprising other cannabinoids. Presently (2015) marijuana growers extract CBD from plants in form of oils or "shatters" that have content of CBD ranging from 25 to 80% by weight of the oil and THC from 10-25% by weight of the oil. Recently, however, due to availability of sophisticated separators, it made possible to obtain pure CBD of 99.9% from hybrid marijuana plants or hemp plans with very low content of THC below 0.1%.

In certain examples, preparation 27 preferably comprises from about one (1) percent to about fifty (50) percent by weight CBD, more preferably from about five (5) to about 30 percent by weight CBD, and more preferably from about 10 to about 20 percent by weight CBD.

In the same or other examples, the preparation 27 comprises a liquid carrier in amounts ranging from about 50 percent to about 99 percent by weight of the preparation 27. Preparation 27 also comprises from about one (1) percent to about ten (10) percent, and preferably about three (3) percent of a gelling agent (preferably hydroxyl propyl cellulose) by weight of the preparation 27. Preparation 27 also includes from zero to about ten (10) percent by weight of at least one penetration enhancer. In certain examples, the liquid carrier comprises at least one polar liquid of the type described previously. Suitable penetration enhancers include 1,2 propylene glycol, dimethyl sulfoxide (DMSO), oleic acid, and isopropyl palmitate (IPP).

When provided as substantially pure CBD, the amount of CBD in preparation 27 by weight of CBD plus liquid carrier(s) (i.e., excluding gelling agents such as cellulose derivatives like hydroxyl propyl cellulose), preferably ranges from about two (2) percent to about 40 percent by weight of the combination of CBD and liquid carrier(s), more preferably from four (4) percent to about 30 percent by weight of the combination of CBD and liquid carrier(s), and still more preferably from about five (5) percent to about 20 percent by weight of the combination of CBD and liquid carrier(s). When CBD is provided as part of a *cannabis* plant oil extract, the concentration of oil in the combination of oil and liquid carrier(s) is preferably from about five (5) percent to about fifteen (15) percent by weight of the combination of oil and liquid carrier(s), more preferably from about eight (8) percent to about thirteen (13) percent by weight of the combination of oil and liquid carrier(s), and still more preferably from about nine (9) to about eleven (11) percent by weight of the combination of oil and liquid carriers(s). Ten percent oil by weight of the combination of oil and liquid carrier(s) is especially preferred.

Suitable backing materials for backing 22 include occlusive polymeric films such as polyethylene, polyethylene terephthalate (PET) and combinations thereof. Although device 20 may include an overlay patch, in preferred examples, one is not provided. In general, an overlay patch is not necessary if the hydrophilic, porous membrane 24 is already coated with skin adhesive 30. If the membrane 24 is not coated with an adhesive (e.g., in order to maximize the flux of CBD into the skin), an overlay patch should be placed over the reservoir 26 in order to ensure intimate contact of the hydrophilic, porous membrane 24 with skin. In certain examples, the skin contact area ("active transdermal flux area") of the membrane 24 of a device 20 is preferably at least about 10 $cm^2$, more preferably at least about 20 $cm^2$, and still more preferably at least about 30 $cm^2$. At the same time, the skin contact area of device 20 is preferably no more than about 30 $cm^2$, preferably no more than about 25 $cm^2$, and still more preferably no more than about 22 $cm^2$. At a given flux rate, the skin contact area may be selected to achieve the desired daily dose of CBD (or the dose over whatever time period is of therapeutic interest). Applicants found the highest transdermal flux of CBD from a formulation that comprises PIB adhesive and 10% CBD. In view of this finding, a preferred embodiment of the patch is a patch measuring 20 $cm^2$ and that would deliver a daily systemic dose of about 5 mg of CBD.

In embodiments, patch measures about 5 $cm^2$, about 6 $cm^2$, about 7 $cm^2$, about 8, about 9, about 10, about 12, about 14, about 15, about 16 $cm^2$, about 18 $cm^2$, about 20 $cm^2$, about 22 $cm^2$, about 24 $cm^2$, about 25 $cm^2$, about 26 $cm^2$, about 28 $cm^2$, about 30 $cm^2$, and the like. These measurements refer to the area of the patch, and do not imply the shape of the patch. In embodiments, patch is square shaped, square shaped with rounded corners, oval shaped, rectangle shaped, rectangle shaped with rounded corners, circular, and so on.

Figure 2:
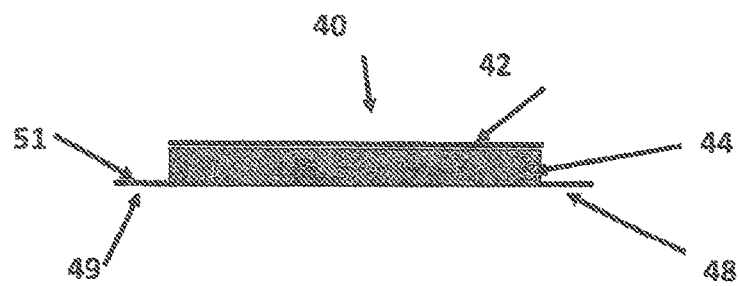
FIG. 2 is a side cross-sectional view of a monolithic-style transdermal device for delivering CBD to a wearer's skin.
Figure 3:
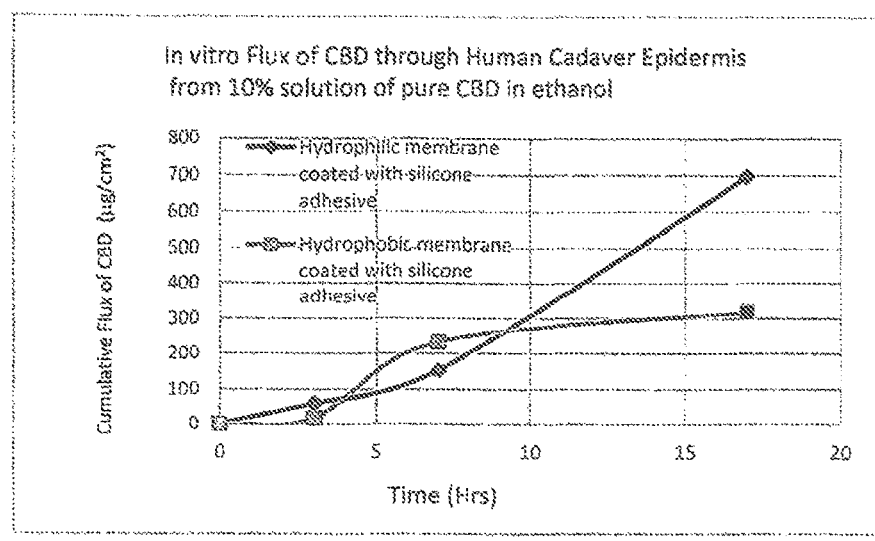
FIG. 3 is a graph depicting the cumulative flux ($\mu g/cm^2$) of CBD with respect to time (hours) through a human cadaver epidermis from a solution comprising ten (10) percent by weight CBD and 90 percent by weight of an ethanol solvent through each of a hydrophilic, microporous membrane and a hydrophobic, microporous membrane; at 17 hours, cumulative flux of CBD through the hydrophilic membrane was about 700 $\mu g/cm^2$.
Figure 4:
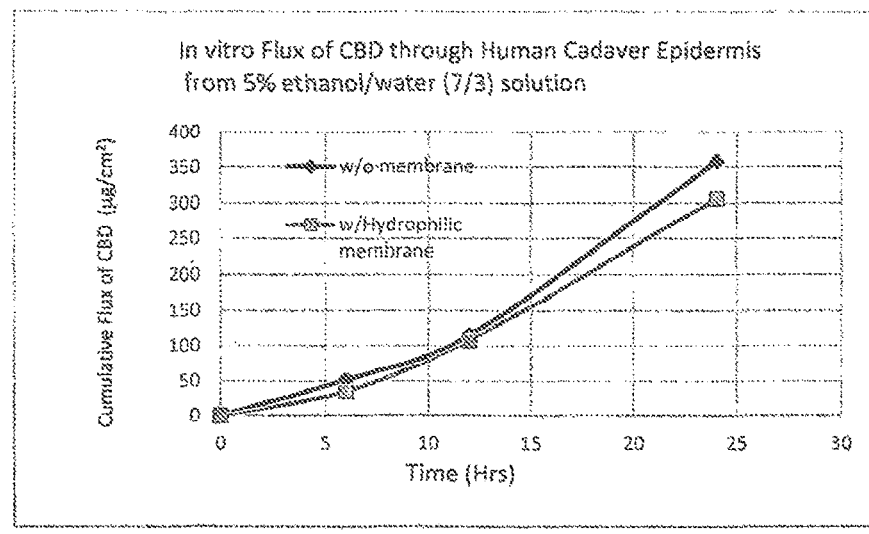
FIG. 4 is a graph depicting the cumulative flux ($\mu g/cm^2$) of CBD with respect to time (hours) through a human cadaver epidermis through a device with a hydrophilic porous membrane and a device lacking such a membrane from a solution comprising five (5) percent by weight of CBD and 90 percent by weight of a solvent comprising 70 percent by weight ethanol and 30 percent by weight water.

Referring to FIG. 2, an example of monolithic-style transdermal drug delivery device 40 for delivering CBD is depicted. Monolithic transdermal device 40 includes a backing 42 of the type described previously with respect to backing 22 of reservoir transdermal device 20. A matrix 44 of skin adhesive mixed with a therapeutically effective amount of CBD is coated on one side of backing 42. The matrix 44 is preferably formulated to adhere the device 20 to the user's skin for a period of no less than about 24 hours while avoiding appreciable skin irritation to the user's skin. A release liner 48 is releasable adhered to matrix 44 on a surface of matrix 44 opposite the surface adhered to backing 42. First side 49 of release liner 48 faces away from matrix 44 and a portion of second side 51 of release liner 48 is adhered to matrix 44. To use the monolithic transdermal device 40, the release liner 48 is peeled away and the exposed surface of adhesive matrix 44 is applied to the skin.

The skin adhesive comprising matrix 44 preferably comprises at least one of an acrylate pressure sensitive adhesive, a polyisobutylene pressure sensitive adhesive, and an amine-compatible silicone pressure sensitive adhesive. Suitable acrylate adhesives include DuroTak 87-2516. Suitable polyisobutylene adhesives include those having a viscosity-average molecular weight ranging from about 30,000 Daltons to about 70,000 Daltons, preferably from about 35,000 Daltons to about 65,000 Daltons, and more preferably from about 40,000 Daltons to about 60,000 Daltons.

In certain preferred examples, matrix 44 preferably comprise a polyisobutylene adhesive having a viscosity-average molecular weight as described above and an adhesion/viscosity modifier. The adhesion/viscosity modifier is preferably a mineral oil or silicone fluid present in an amount ranging from about one (1) to about ten (10) percent by weight of matrix 44, more preferably from about two (2) to about six (6) percent by weight of matrix 44, and still more preferably from about three (3) to about four (4) percent by weight of the matrix 44. Mineral oils that are suitable for use as the adhesion/viscosity modifier have a molecular weight ranging from 100 to about 1000 Daltons, more preferably from about 200 to about 600 Daltons, even more preferably from about 350 Daltons to about 450 Daltons, and still more preferably about 400 Daltons. Silicone fluids that are suitable for use as the adhesion/viscosity modifier preferably comprise —OH end-capped polydimethylsiloxanes having a kinematic viscosity at 20° C. ranging from about 100 cSt to about 1000 cSt. Commercially available silicone fluids that may be used as the adhesion/viscosity modifier include the Dow Corning Q7-9120 fluids, which are available in kinematic viscosities (at 20° C.) of 20, 100, 350, 1000, and 12,500 cSt. In preferred examples of silicone adhesion/viscosity modifier, the Q7-9120 100 cSt or 1000 cSt (or mixtures thereof) are used.

Preferred polyisobutylene adhesives are not supplied with mineral oil. In certain preferred examples, the polyisobutylene component of matrix 44 is a Vistanex LM polyisobutylene adhesive. In other preferred examples, the polyisobutylene component of matrix 44 is an Oppanol B13 polyisobutylene adhesive supplied by BASF.

In yet another example, the adhesive component of matrix 44 may comprise a blend of acrylic adhesive and polyisobutylene adhesive, and preferably, a blend of an acrylic adhesive and a polyisobutylene adhesive having the viscosity-average molecular weight described above (from about 30,000 Daltons to about 70,000 Daltons, preferably from about 35,000 Daltons to about 65,000 Daltons, and more preferably from about 40,000 Daltons to about 60,000 Daltons). When acrylic adhesives are combined with such polyisobutylene adhesives, the amount of acrylic adhesive by weight of the total amount of adhesive in matrix 44 is preferably from about one (1) to about 50 percent. In one example, the adhesive component of matrix 44 comprises 80 percent Oppanol B13 by weight of the total amount of adhesive in matrix 44 and twenty (20) percent Durotak 87-2516 by weight of the total amount of adhesive in matrix 44.

In examples in which matrix 44 comprises an amine-compatible silicone adhesive, the amine-compatible silicone adhesive is preferably of the type described previously with respect to skin adhesive 30 of reservoir transdermal device 20.

The amount of CBD in the matrix 44 preferably ranges from about one (1) to about 30 percent by weight of the matrix 44, more preferably from about two (2) percent to about 25 percent by weight of the matrix 44, and still more preferably from about five (5) percent to about twenty (20) percent by weight of the matrix 44. In those cases where pure CBD is used in matrix 44, the amount of pure CBD by weight of matrix 44 is preferably from about two (2) percent to about twenty (20) percent, more preferably from about four (4) percent to about fifteen (15) percent, and still more preferably from about five (5) percent to about ten (10) percent.

When CBD is provided as part of a *cannabis* plant oil extract, the amount of oil by weight of matrix 44 is preferably from about fifteen (15) percent to about 40 percent by weight, preferably from about twenty (20) percent to about 30 percent by weight, and still more preferably from about 24 percent to about 26 percent by weight.

In certain preferred examples wherein CBD is provided as part of a *cannabis* plant oil extract, the oil further comprises rosins and/or terpenes that remain present after extraction. It has been found that these rosins and terpenes improve adhesion to the skin. Thus, the use of plant extract oils in monolithic device 40 provides a synergistic effect in both allowing for transdermal delivery of CBD and providing a device 40 that can withstand showers and minor brushings over the worn device 40 for many days.

Monolithic device 40 may also include penetration enhancers, including but not limited to oleic acid, isopropyl palmitate (IPP), DMSO, 1,2 propylene glycol, and isopropyl myristate (IPM). The amount of penetration enhancer preferably ranges from zero to about ten (10) percent by weight of the matrix 44.

In certain examples, the skin contact area of device 20 is preferably at least about 10 $cm^2$, more preferably at least about 15 $cm^2$, and still more preferably at least about 18 $cm^2$. At the same time, the skin contact area of device 20 is preferably no more than about 30 $cm^2$, preferably no more than about 25 $cm^2$, and still more preferably no more than about 22 $cm^2$. At a given flux rate, the skin contact area may be selected to achieve the desired daily dose of CBD (or the dose over whatever time period is of therapeutic interest).

Terpenes.

In embodiments, the present disclosure encompasses one or more non-cannabinoid terpenes. See, US 2015/0080265 of Elzinga and Raber and US2015/0152018 of Raber and Elzinga, each of which is incorporated by reference in their entirety.

Preferred Embodiments

In a preferred embodiment, device comprises a transdermal monolithic patch formulation with CBD in PIB adhesive, from 1% to 30%, from 5%-30%, from 10%-30%, from 15%-30%, from 20%-30%, from 25%-30%, or alternatively, from 1% to 25%, from 5%-25%, from 10%-25%, from 15%-25%, from 20%-25%, or alternatively, from 1% to 20%, from 5%-20%, from 10%-20%, from 15%-20%, or alternatively, from 1% to 15%, from 5%-15%, from 10%-15%, or alternatively, from 1% to 10%, from 2% to 10%, from 5% to 10%, and the like.

In a preferred embodiment, device comprises transdermal monolithic patch formulation with CBD NB adhesive with CBD concentration in solid adhesives from 1% to 30% and penetration enhancers in range of 0% to 10% In another preferred embodiment, device comprises transdermal patch formulation comprising a reservoir in the shape of a "ravioli" constructed with microporous hydrophilic or hydrophobic membrane on one side and occlusive film on other side.

In embodiments, device comprises transdermal reservoir patch formulation as thixotropic alcohol or alcohol/water solution gelled with hydroxyalkyl cellulose containing CBD at high concentration ranging from 1% to 50% CBD Moreover, device comprises transdermal reservoir patch formulation comprising a reservoir containing thixotropic alcohol or alcohol/water solution gelled with hydroxyalkyl cellulose and containing CBD at a high concentration, ranging from 1% to 50% and skin penetration enhancers in a concentration range of 0% to 10%.

What is also encompassed, is transdermal patch formulation comprising a reservoir in shape of "ravioli" constructed with microporous hydrophilic or hydrophobic membrane on one side and occlusive film on other side where the microporous membrane is coated with thin layer of silicone adhesive. In delivery embodiments, reservoir patch of 20 cm$^2$ is capable of systemically delivering CBD at about 0.5 mg/day, about 1.0 mg/day, about 1.5 mg/day, about 2.0 mg/day, about 5.0 mg/day, about 10 mg/day, about 15 mg/day, about 20 mg/day, about 25 mg/day, about 30 mg/day, about 35 mg/day, about 40 mg/day, and the like.

In other delivery embodiments, reservoir patch of 20 cm$^2$ is capable of systemically delivering CBD at least 0.5 mg/day, at least 1.0 mg/day, at least 1.5 mg/day, at least 2.0 mg/day, at least 5.0 mg/day, at least 10 mg/day, at least 15 mg/day, at least 20 mg/day, about 25 mg/day, about 30 mg/day, at least 35 mg/day, at least 40 mg/day, and so on.

CBD delivered by patch formulations through skin is safer because it circumvents the gastric system and liver first-pass, avoiding toxic side effects and increasing bioavailability of the compound. Also, CBD delivered by patch formulation has better patient compliance in comparison to pills, edibles, tinctures, and creams.

Exclusionary Embodiments

In device embodiments, a device of the present disclosure is substantially free of all cannabinoids that are not CBN. In composition embodiments, a composition of the present disclosure is substantially free of all cannabinoids that are not CBN.

In device embodiments, a device of the present disclosure is substantially free of one or more of tetrahydrocannabinol (THC), tetrahydrocannabinolic acid (THC-a), cannabinol (CBN), and cannabichromene (CBC). Also, a device of the present disclosure is substantially free each and every one of tetrahydrocannabinol (THC), tetrahydrocannabinolic acid (THC-a), cannabinol (CBN), and cannabichromene (CBC). In composition embodiments, a composition of the present disclosure is substantially free of one or more of tetrahydrocannabinol (THC), tetrahydrocannabinolic acid (THC-a), cannabinol (CBN), and cannabichromene (CBC). Also, a composition of the present disclosure is substantially free each and every one of tetrahydrocannabinol (THC), tetrahydrocannabinolic acid (THC-a), cannabinol (CBN), and cannabichromene (CBC).

In one aspect, the term "substantially free" can mean that the quantity of one or more of THC, THC-a, CBN, and CBC, occurs at a molar quantity that is under 20%, under 15%, under 10%, under 5%, under 4%, under 2%, under 1%, under 0.5%, under 0.1%, under 0.05%, or under 0.01%, that of CBD. In another aspect, the term "substantially free" can mean that the quantity of each and every one of THC, THC-a, CBN, and CBC, occurs at a molar quantity that is under 20%, under 15%, under 10%, under 5%, under 4%, under 2%, under 1%, under 0.5%, under 0.1%, under 0.05%, or under 0.01%, that of CBD.

The following methods of measurement take into account the physical nature of a composition and the physical nature of the container or matrix that comprises a composition. In measuring a composition that is "substantially free," what can be measured is all compounds that are comprised by the composition, where the composition takes the form of an oil, a paste, a slurry, an adhesive, a powder, a solution, and the like, or that takes the form of a matrix, a reservoir, and impregnated fabric, a flask, a conduit, that holds, contains, absorbs, adsorbs, and the like, the oil, a paste, a slurry, an adhesive, a powder, a solution, and the like.

Without implying any limitation, the present disclosure can exclude a composition that comprises one or more of the following compounds, and can also exclude a device that comprises one or more of the following compounds. What can be excluded is a compound that is, buprenorphine, clonidine, estradiol, fentanyl, granisetron, methylphenidate, nitroglycerin, oxybutynin, scopolamine, selegiline, testosterone, a vaccine, influenza virus vaccine, a mammalian hormone, a synthetic analogue of a mammalian hormone, a chemically modified mammalian hormone, lidocaine, estrogen, salicyclic acid, a contraceptive, rivastigmine, rotogotine, tulobuterol, adrenergic agonist, cholinesterase inhibitor, dopamine receptor agonist, oxybutynin, bupropion, varenicline, nicotine, antidepressant, smoking cessation drug, cholinsterase inhibitor, methylphenidate, buprenorphine, opioid analgesic agent, sumatriptan, antiviral drug, anti-retrovirus drug, mammalian steroid, chemical analogue of mammalian steroid, drug for attention-deficit hyperactivity disorder, and so on.

In embodiments, the present disclosure can exclude a reservoir-type device where backing does not directly contact reservoir; or where reservoir does not directly contact a hydrophilic porous membrane; or where hydrophilic porous membrane does not directly contact a release liner; or where reservoir does not contain all of: (1) a liquid carrier, (2) a gelling agent, and (3) CBD. Also, what can be excluded is a reservoir-type device that does not comprise all of the above.

In embodiments, what can be excluded is an adhesive polymer, or a device comprising an adhesive polymer, where the adhesive polymer reacts with amines. Also what can be excluded, is an adhesive polymer, or a device comprising an adhesive polymer, where the adhesive polymer has any free hydroxyl groups, where the adhesive polymer has over 1 free hydroxyl groups per 100 atoms of the adhesive polymer, where the adhesive polymer has over 5 free hydroxyl groups per 100 atoms of the adhesive polymer, where the adhesive polymer has over 10 free hydroxyl groups per 100 atoms of the adhesive polymer, where the adhesive polymer has over 20 free hydroxyl groups per 100 atoms of the adhesive polymer, and so on. For this exclusionary embodiment, the skilled artisan understands that any polymer consists of a large number of atoms, for example, about five thousand atoms.

In embodiments, what can be excluded is a monolith-type device where a backing is not in direct contact with a matrix of skin adhesive; where matrix of skin adhesive is not in direct contact with a releasable liner; where matrix does not comprise CBD; or all of the above.

What can also be excluded is a preparation, or a device comprising a preparation, where the preparation has over 1% gelling agent, over 2%, over 3%, over 4%, over 5%, over 6%, over 7%, over 8%, over 9%, over 10%, over 12%, over 14%, or over 16%, of gelling agent. Also, what can be excluded is a preparation, or a device comprising a preparation, where the preparation has under 1% gelling agent, under 2%, under 3%, under 4%, under 5%, under 6%, under 7%, under 8%, under 9%, under 10%, under 12%, under 14%, or under 16%, of gelling agent.

What can also be excluded is a preparation, or a device comprising a preparation, where the preparation has over 1% penetration enhancer, over 2%, over 3%, over 4%, over 5%, over 6%, over 7%, over 8%, over 9%, over 10%, over 12%, over 14%, or over 16%, of penetration enhancer. Also, what can be excluded is a preparation, or a device comprising a preparation, where the preparation has under 1% penetration enhancer, under 2%, under 3%, under 4%, under 5%, under 6%, under 7%, under 8%, under 9%, under 10%, under 12%, under 14%, or under 16%, of penetration enhancer.

In other embodiments, what can be excluded is a preparation, a composition, a device comprising a preparation, a device comprising a composition, where said preparation or composition has a CBD (or THC, or combined weight of CBD and THC) content by weight of under 1%, under 2%, under 3%, under 4%, under 5%, under 6%, under 8%, under 10%, under 12%, under 14%, under 16%, under 18%, under 20%, under 25%, under 30%, under 35%, under 40%, under 45%, under 50%, under 55%, under 60%, under 65%, under 70%, under 75%, and so on. Also, what can be excluded is a preparation, a composition, a device comprising a preparation, a device comprising a composition, where said preparation or composition has a CBD (or THC, or combined weight of CBD and THC) content by weight that is greater than 5%, greater than 6%, greater than 7%, greater than 8%, greater than 10%, greater than 12%, greater than 14%, greater than 16%, greater than 18%, greater than 20%, greater than 25%, greater than 30%, greater than 35%, greater than 40%, greater than 45%, greater than 50%, greater than 55%, greater than 60%, greater than 65%, greater than 70%, and so on. In embodiments, what can be excluded is a preparation, a composition, a device comprising a preparation, or a device comprising a composition, where the percent by weight is defined by one or more of the above "under" or "greater than" parameters. "Composition" can refer to, for example, matrix of a skin adhesive, or to fluid in hydrophilic porous membrane, and so on. Alternatively, the present disclosure can comprise one or more of the above compositions, as set forth by "under" parameters or "greater than" parameters.

Moreover, in embodiments what can be excluded is any device that does not include an occlusive system polymer film, that does not include a polyethylene occlusive polymer film, that does not include a PET occlusive polymer film, that does not include an occlusive polymer film made of both polyethylene and PET. Also, what can be excluded is a device that has an overlay patch, and a device that does not comprise an overlay patch.

In embodiments, polar organic liquid can comprise, or can exclude, one or more of methanol, ethanol, propanol, isopropanol, butanol, pentanol, acetic acid, propionic acid, butyric acid, valeric acid, caproic acid, caprylic acid, capric acid, lauric acid, myristic acid palmitic acid, stearic acid, palmitoleic acid, oleic acid, linoleic acid, linolenic acid, linear alkanes of 5, 6, 7, 8, 9, 10, 11, 12, 13, 14, 15, 16, 17, 18, 19, 20, 21, 22, 23, 24, or more carbons, branched chain alkanes with a backbone of 5, 6, 7, 8, 9, 10, 11, 12, 13, 14, 15, 16, 17, 18, 19, 20, 21, 22, 23, 24, or more carbons, linear alkenes (olefins) of 5, 6, 7, 8, 9, 10, 11, 12, 13, 14, 15, 16, 17, 18, 19, 20, 21, 22, 23, 24, or more carbons, branched chain alkenes (olefins) with a backbone of 5, 6, 7, 8, 9, 10, 11, 12, 13, 14, 15, 16, 17, 18, 19, 20, 21, 22, 23, 24, or more carbons, and so on. Alternatively, the present disclosure can comprise one or more of the above polar organic liquids.

Example 1

The effects of using a hydrophobic, porous membrane versus a hydrophilic, porous membrane (such as membrane 24) in reservoir transdermal device 20 are studied in this example. A mixture is formed by dissolving CBD powder in ethanol to yield a solution comprising 10 percent by weight CBD and 90 percent by weight ethanol. The backing 22 is an occlusive backing film (PE/PET from 3M). Hydroxy ethyl cellulose is added to the solution to yield a thixotropic preparation 27. A volume of 300 µL of the preparation is placed in the reservoir 26.

The skin adhesive 30 is a BIO PSA 7-4301 adhesive coated to a thickness of 15 g/m$^2$ on side 36 of membrane 24. An overlay adhesive patch is placed over the reservoir which forms an island in the middle. The overlay assures adhesion of the reservoir to the skin. The device 20 is contacted with a human cadaver epidermis, and diffusion through the epidermis is measured using the Franz Diffusion Cell method.

In a first run, membrane 24 is a Lydall® Evopor™ 5E02A, hydrophilic, microporous membrane (of 0.2 µm pore size). In a second run, the device 20 is constructed similarly, but membrane 24 is a hydrophobic Lydall® Solupor™ 7P03A porous membrane. As FIG. 3 indicates, after a period of about 9 hours, the device 20 with the hydrophilic membrane provides a monotonically increasing cumulative flux of CBD through the cadaver skin which significantly exceeds the cumulative flux of CBD from the hydrophobic membrane device, which becomes asymptotic at about 300 µg/cm$^2$.

Example 2

The reservoir device 20 of Example 1 is used, but instead of using ethanol alone as the liquid carrier, a mixture of ethanol and water is used wherein the ethanol comprises 70 percent by weight of the ethanol/water mixture, and water comprises 30 percent by weight of the ethanol/water mixture. The amount of CBD by weight of the combination of CBD and ethanol/water is 5 percent, and the amount of ethanol/water is 91.5 percent. The gelling agent is hydroxyethylcellulose, which is present in an amount of about 3.5% by weight of the preparation 27. A first run is conducted in which the membrane is placed comprises CBD is present.

The device 20 is contacted with a human cadaver epidermis, and diffusion through the epidermis is measured using the Franz Diffusion Cell method. In a first run, the hydrophilic, porous membrane 24 of Example 1 is used. In a second run, the membrane 24 is omitted so that CBD diffuses directly through the skin adhesive 30. The cumulative flux versus time is plotted in FIG. 4, which indicates that the permeability of CBD through the skin is the same regardless of whether the membrane 24 is provided. It is also discovered that an overlay patch (not shown in FIG. 1) is not required to hold device 20 on the skin.

Example 3

This example is conducted using three reservoir transdermal devices such as those of Example 1, with each having the hydrophilic, porous membrane described therein. In each case, the preparation includes a mixture of CBD and a liquid carrier with ten (10) percent CBD by weight of the CBD/liquid carrier mixture. Three runs are conducted, each with a device that includes a different liquid, carrier in its preparation 27: 1,2 propylene glycol, PEG-300, and oleic acid. Diffusion through a human cadaver epidermis is measured using the Franz Diffusion Method.

Figure 5:
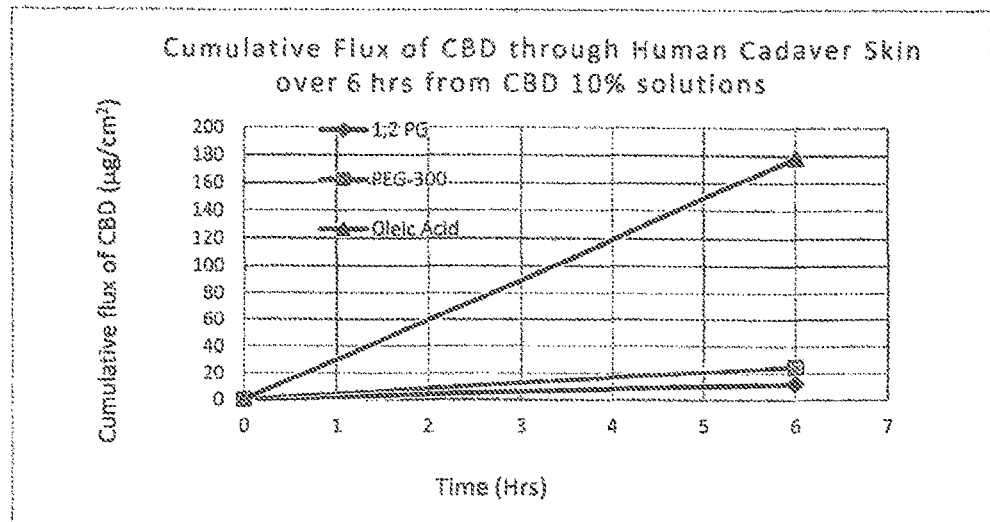
FIG. 5 is a graph depicting the cumulative flux ($\mu g/cm^2$) of CBD through a human cadaver epidermis over a six hour period from solutions comprising ten (10) percent by weight CBD and 90 percent by weight of one of three liquid carriers.

The cumulative flux versus time is plotted in FIG. 5. As the figure indicates, throughout the period, oleic acid provides a significantly better rate of transfer of CBD through the skin than either 1,2 propylene glycol or PEG-300.

Example 4

Figure 6:
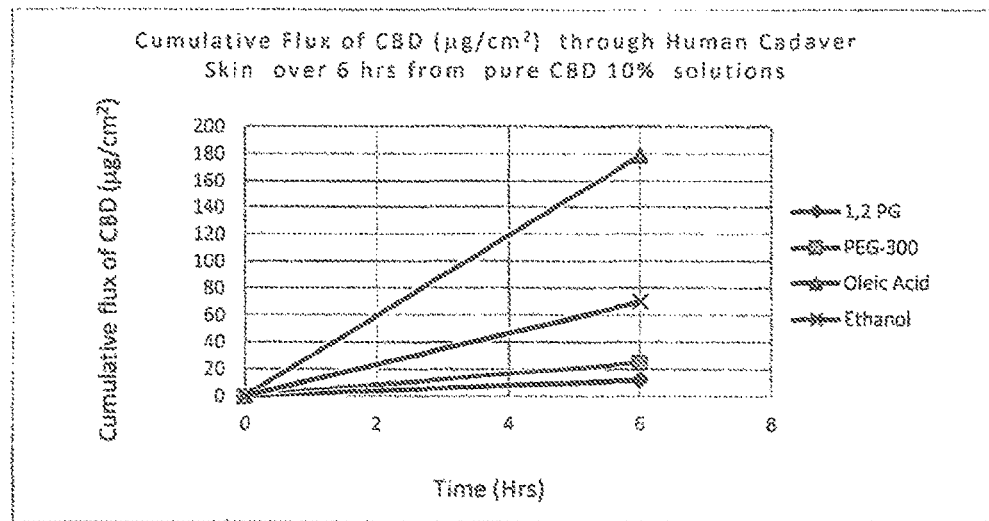
FIG. 6 is a graph depicting the cumulative flux ($\mu g/cm^2$) of CBD through a human cadaver epidermis over a six hour period from solutions comprising ten (10) percent by weight CBD and 90 percent by weight of one of four liquid carriers.

This example is similar to Example 3, except that an ethanol carrier is also tested. As indicated in FIG. 6, ethanol shows superior transfer of CBD through the skin relative to 1,2 propylene glycol and PEG-300. However, oleic acid provides superior transfer relative to all three of the other liquid carriers.

Example 5

Figure 7:
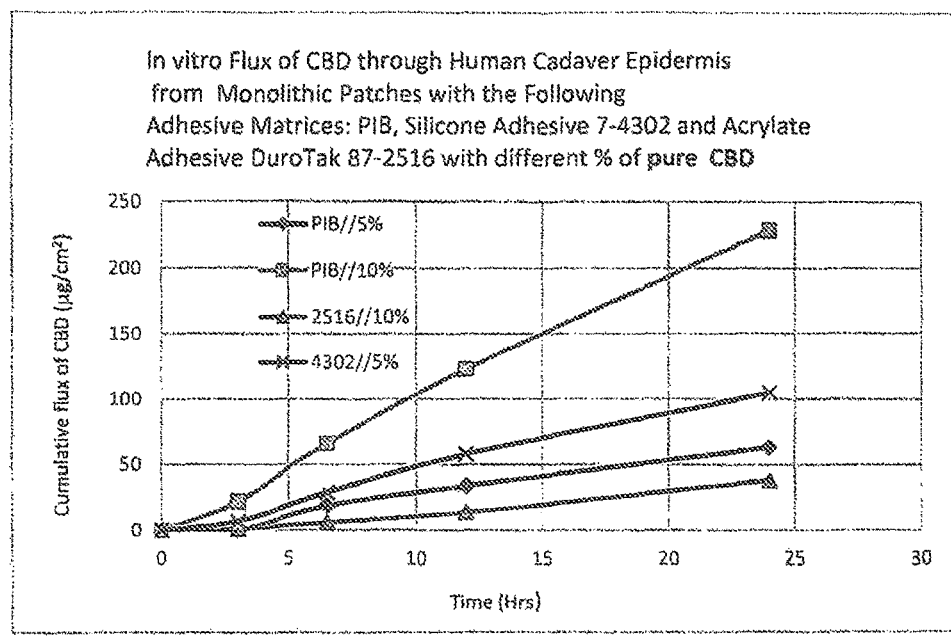
FIG. 7 is a graph depicting the cumulative flux ($\mu g/cm^2$) of CBD through a human cadaver epidermis from a monolithic adhesive matrix comprising varying amounts (weight percent) of three different adhesives and varying amounts (weight percent) of CBD comprising 45.3 percent by 33.5 percent by weight THC.

A monolithic transdermal device 40 is constructed using a matrix 44 of pure CBD and three different adhesives. A first device 40 includes a PE/PET backing and a matrix 44 comprising 95 percent Vistanex LM polyisobutylene adhesive by weight of matrix 44 mixed with 5 percent substantially pure CBD by weight of matrix 44. A second device is similarly constructed, but the amount of CBD in the matrix 44 is 10 percent by weight of the matrix 44, and the amount of Vistanex LM is 90 percent by weight of the matrix 44. A third patch is constructed using a DuroTak 87-2516 adhesive in an amount of 90 percent by weight of matrix 44 and 10 percent CBD by weight of matrix 44, and a fourth patch is constructed using a BIO PSA 7-4302 adhesive in an amount of 95 percent by weight of matrix 44 and 5 percent CBD by weight of matrix 44. As indicated in FIG. 7, the Vistanex LM/10 percent CBD device provides superior CBD transfer through the epidermis relative to the three other devices.

Example 6

Three monolithic devices are constructed similar to those of Example 5. However, instead of pure CBD, a *cannabis* extract oil comprising 45.3 percent CBD and 33.5% THC is mixed with the adhesive to form the adhesive matrix 44. In each device, the amount of oil in the matrix 44 is 25 percent by weight of the matrix 44. The matrix 44 in the first device comprises 75 percent by weight BIO PSA 7-4302. The matrix 44 in the second device comprises 75 percent by weight Vistanex LM, and the matrix 44 in the third device comprises 75 percent by weight DuroTak 87-2516. PIB is polyisobutylene. PIB is a vinyl polymer that is made from the monomer isobutylene (IB) by cationic polymerization (Benedek, I and Feldstein, M M (eds.) Technology of Pressure-Sensitive Adhesives and Products. Chapter 4 by Willenbacher, N. and Lebedeva, O V. CRC Press (2009).

Notably, from a 20 cm² reservoir device using a liquid carrier comprising ethanol and a CBD concentration of 10 weight percent (where 20 cm² is the skin contact area), the expected daily dose of CBD is 30 mg, which is six times higher than the expected dose from a monolithic patch of the same skin contact area.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

SUMMARY

Figure 8:
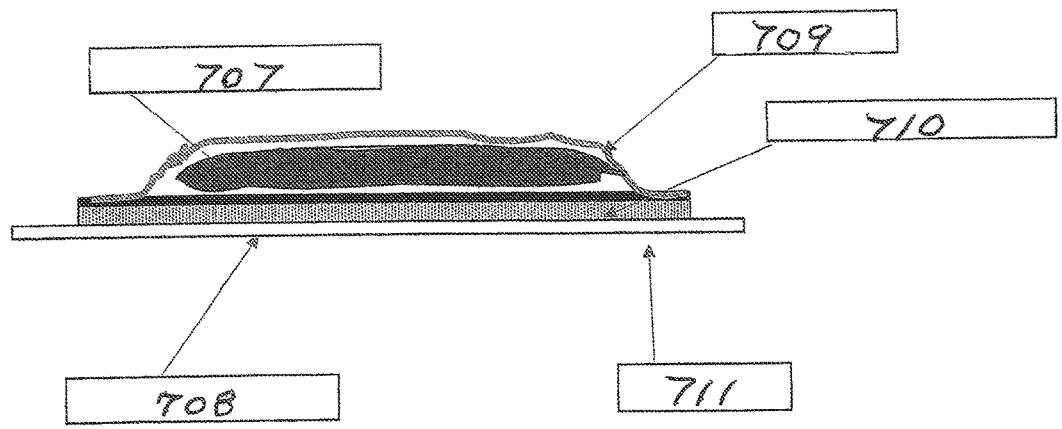
FIG. 8 shows another point of novelty namely the transdermal patch of the reservoir type.

How the reservoir patch formulation works:
Transdermal delivery of CBD from a saturated ethanol solution was found to be significantly higher than the delivery from the monolithic patch (FIG. 2.)
From a 20 cm² reservoir patch we predicted the transdermal daily dose of CBD to be approximately 30 mg, which is six times higher than from the monolithic patch of the same skin contact area.
Referring to FIG. 8, as known to those skilled in the art, construction of the transdermal patch of reservoir type is done by combining 707 CBD in ethanol solution, combined with 708 skin contact adhesive, and 709 occlusive film, 710 microporous membrane and 711 release film, all function together so that the reservoir/ravioli patch can elute actives, as modulated by CBD as discussed herein and claimed below.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A transdermal monolithic patch comprising,
a matrix comprising cannabidiol (CBD) in polyisobutylene (PIB) adhesive, and 1,2-propylene glycol;
a release liner; and
a backing,
wherein the matrix has a first surface adhered to the backing, and a second surface opposite the surface adhered to the backing;
wherein the release liner is adhered to the surface of the matrix opposite the surface adhered to the backing;
wherein the CBD is present in the matrix at concentration from 1% to 30% by weight;
wherein the CBD is dissolved in heptane or ethyl acetate; and
wherein the matrix excludes ethanol.

2. A transdermal monolithic patch comprising,
a matrix comprising cannabidiol (CBD) in amine-compatible silicone adhesive and ethyl acetate, and 1,2-propylene glycol, wherein OH groups of the silicone are capped with methyl groups, wherein the CBD is present in the matrix at a concentration from 1% to 30% by weight, and wherein the matrix excludes oleic acid;
a release liner; and
a backing,
wherein the matrix has a first surface adhered to the backing, and a second surface opposite the surface adhered to the backing; and
wherein the release liner is adhered to the surface of the matrix opposite the surface adhered to the backing.

3. A reservoir patch device for the transdermal delivery of cannabidiol and other moieties,
comprising, in combination:
a backing attached to a hydrophilic, porous membrane to define an enclosed reservoir between the backing and the hydrophilic, porous membrane, wherein the porous membrane has a first side with a skin adhesive and a second side facing the interior of the reservoir;
a preparation comprising a therapeutically effective amount of cannabidiol (CBD) and an organic polar liquid carrier contained in the reservoir, wherein the polar liquid carrier excludes either ethanol or oleic acid, wherein the preparation includes tetrahydrocannabinol (THC), tetrahydrocannabinolic acid (THC-a), cannabinol (CBN), and cannabichromene (CBC);
a release liner attached to the first side of the hydrophilic porous membrane, wherein the release liner is selectively removable from the first side of the hydrophilic porous membrane to expose the skin adhesive, wherein said hydrophilic porous membrane is capable of providing a monotonically increasing cumulative flux of CBD through cadaver skin, which at about 17 hours is 700 micrograms CBD per $cm^2$.

4. The device of claim 3, wherein the skin adhesive is an amine-compatible, silicone adhesive.

5. The device of claim 4, wherein the amine-compatible silicone adhesive comprises trimethylsiloxy end groups that are substantially non-reactive with amines.

6. The device of claim 5, wherein the amine-compatible silicone adhesive comprises a trimethylsiloxy end-capped reaction product of a silanol endblocked polydimethylsiloxane with a silicate resin.

7. The device of any of the preceding claims, wherein the amount of the polar organic liquid carrier by weight of the total amount of the polar liquid organic carrier and cannabidiol in the preparation is at least fifty percent.

8. The device of claim 7, wherein the amount of the skin adhesive per square meter of the porous, hydrophilic membrane is at least 10 grams.

9. The device of claim 3, wherein the preparation comprises a rosin, and wherein the skin adhesive is an amine-compatible silicone skin adhesive with trimethylsiloxy end-capped reaction product of a silanol end-blocked polydimethylsiloxane and a silicate resin.

10. The device of claim 3, wherein the preparation comprises one or more non-cannabinoid terpenes.

11. A monolithic patch device for the transdermal delivery of cannabidiol (CBD), comprising:
a backing;
a matrix that comprises a mixture of an adhesive and a therapeutically effective amount of cannabidiol coated on the backing,
wherein the adhesive comprises a amine-compatible silicone adhesive in ethyl acetate with a solids content of 60 percent by weight and a viscosity of 1200 mPa-s at 20 degrees C., and the mixture has a first surface adhered to the backing and a second, skin-adhering surface;

wherein what is excluded is silicone adhesive polymer that has over 1 free hydroxyl groups per 100 atoms of the adhesive polymer, a release liner removably attached to the second, skin adhering surface of the mixture, and wherein the amine-compatible silicone adhesive comprises trimethylsiloxy end groups that are substantially non-reactive with amines, and wherein 25% of the matrix by weight comprises a *cannabis* extract oil that comprises 45.3 percent CBD and 33.5 percent THC, and wherein 75% of the matrix by weight is the amine-compatible silicone adhesive, wherein the matrix comprises 1,2-propylene glycol.

12. The monolithic patch device of claim 11, wherein the matrix comprises vitamin B12.

13. The monolithic patch device of claim 11, wherein the matrix comprises beta-caryophyllene.

14. A device for the transdermal delivery of cannabidiol (CBD), comprising:
a backing;
a release liner;
a mixture of an adhesive and a therapeutically effective amount of cannabidiol coated on the release liner, wherein the mixture includes tetrahydrocannabinol (THC), tetrahydrocannabinolic acid (THC-a), cannabinol (CBN), and cannabichromene (CBC); wherein the adhesive consisting essentially of a polyisobutylene adhesive not in mineral oil having a viscosity-average molecular weight ranging from about 30,000 Daltons to about 70,000 Daltons, and the mixture has a first surface adhered to the backing and a second, skin-adhering surface to which the release liner is removably adhered, wherein the device excludes ethanol, and wherein the cannabidiol is dissolved in heptane or ethyl acetate.

15. The device of claim 14, wherein the adhesive has a viscosity at 20° C. ranging from about 1000 mPa-s to about 3000 mPa-s.

16. The device of claim 15, wherein the mixture comprises a rosin.

17. The device of claim 16, wherein the mixture comprises one or more non-cannabinoid terpenes.

18. The device of claim 14, wherein the mixture comprises a rosin and one or more non-cannabinoid terpenes.

19. The device of claim 18, wherein the mixture further comprises an adhesion/viscosity modifier comprises a mineral oil having a molecular weight of from about 350 to about 450 Daltons.

20. The device of claim 18, wherein the mixture further comprises adhesion/viscosity modifier comprises a silicone fluid having a kinematic viscosity at 20° C. ranging from about 100 cSt to about 1000 cSt.

21. The device of claim 20, wherein the silicone fluid is a hydroxyl end-capped polydimethylsiloxane.

22. The device of claim 6, wherein the hydrophilic, porous membrane has a mean flow pore size of at least 0.02 microns.

23. The device of claim 3, wherein the microporous hydrophilic membrane has a hydrophilic content that is at least 2 weight percent based on the total dry weight of the membrane, and wherein the microporous hydrophilic membrane comprises poly(ethylvinyl) alcohol hydrophilic component.

* * * * *